Figure 1:
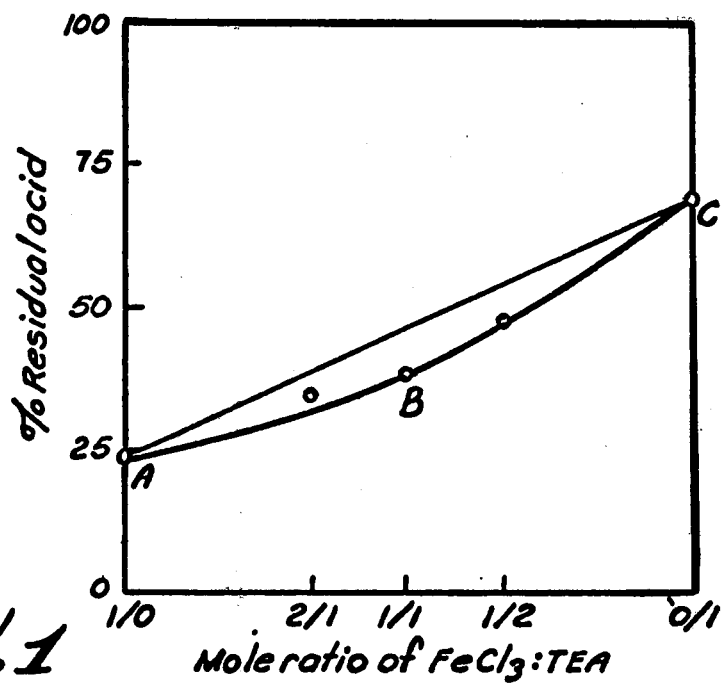

United States Patent [19]

Gurgiolo

[11] 4,069,242
[45] Jan. 17, 1978

[54] PROCESS FOR PREPARATION OF β-HYDROXY ESTERS BY REACTION OF ORGANIC CARBOXYLIC ACIDS AND VICINAL EPOXIDES

[75] Inventor: Arthur E. Gurgiolo, Lake Jackson, Tex.

[73] Assignee: The Dow Chemical Company, Midland, Mich.

[21] Appl. No.: 179,166

[22] Filed: Sept. 9, 1971

Related U.S. Application Data

[63] Continuation-in-part of Ser. No. 797,184, Feb. 6, 1969, abandoned.

[51] Int. Cl.² ........................................... C07C 67/26
[52] U.S. Cl. ................................... 560/93; 260/410.6; 260/408; 260/410.5; 560/240; 560/209; 560/200; 560/112; 560/105; 560/1; 560/192; 560/71; 560/64; 560/189; 252/428; 252/429 B; 252/431 C; 252/431 N
[58] Field of Search ............. 260/486 B, 475 P, 410.6, 260/496, 485 G

[56] References Cited

U.S. PATENT DOCUMENTS

| 2,910,490 | 10/1959 | Malkemus | 260/410.6 |
| 2,929,835 | 3/1960 | Hayes et al. | 260/486 |
| 3,399,229 | 8/1968 | Kunze et al. | 260/485 |
| 3,641,112 | 2/1972 | Ichikawa et al. | 260/475 P |
| 3,873,602 | 3/1975 | Katzakian, Jr. et al. | 260/475 P |

FOREIGN PATENT DOCUMENTS

| 1,003,346 | 9/1965 | United Kingdom. |
| 871,767 | 6/1961 | United Kingdom. |

OTHER PUBLICATIONS

Mikulasova et al., Chemical Abstracts, vol. 61, 16,242de (1964).
Asahara et al., Chemical Abstracts, vol. 62, 1554a (1965).
Schaefer et al., Chemical Abstracts, vol. 68, 39075g (1968).

*Primary Examiner*—Donald G. Daus
*Assistant Examiner*—D. Rivers
*Attorney, Agent, or Firm*—L. Wayne White

[57] ABSTRACT

A synergistic catalytic effect is realized in the esterification reaction between an organic carboxylic acid and a vicinal epoxide by using a catalyst system comprising: (a) a compound containing an amino and/or ammonium nitrogen atom, in combination with (b) a soluble compound containing an ionizable atom of iron or chromium.

16 Claims, 2 Drawing Figures

PROCESS FOR PREPARATION OF β-HYDROXY ESTERS BY REACTION OF ORGANIC CARBOXYLIC ACIDS AND VICINAL EPOXIDES

CROSS-REFERENCE TO RELATED APPLICATION

This is a continuation-in-part application of Ser. No. 797,184 filed Feb. 6, 1969 now abandoned.

BACKGROUND OF THE INVENTION

The reaction between an organic carboxylic acid and a vicinal epoxide to yield the corresponding β-hydroxy ester is known to be catalyzed by inorganic bases and by amino compounds, e.g. U.S. Pat. No. 2,929,835.

Such a reaction is also known to be catalyzed by compounds containing an ionizable atom of iron or chromium. Illustrative of such compounds is ferric chloride, ferric alcoholates or carboxylates and chromium tribromide, and other like compounds, as described in British Pat. No. 871,767.

The reaction conditions of temperature, pressure, etc., may vary with reactants, but generally, the temperature is between about 60° C. and 130° C., and the pressure is atmospheric or superatmospheric, and the procedure involves mixing the reactants in the presence of a suitable catalyst and then maintaining the reaction mixture at a suitable temperature and pressure until the desired reaction product is formed.

SUMMARY OF THE INVENTION

It has now been discovered that a synergistic catalytic effect is realized in the esterification reaction between an organic carboxylic acid and a vicinal epoxide by using a catalyst system comprising: (a) a compound containing an amino and/or ammonium nitrogen atom, in combination with (b) a soluble compound containing an ionizable atom of iron or chromium.

By synergistic catalytic effect is meant that the total catalytic effect realized in the reaction by using the subject catalyst system, i.e., an amino catalyst in combination with an iron or chromium catalyst, is greater than the theoretical sum of the catalytic effects of the amino catalyst and the iron or chromium catalyst used separately. Accordingly, the subject catalyst system has an unexpectedly favorable effect on the reaction rate and also on the product yield.

Suitable amine compounds are those of the known class of catalytic compounds containing an amino and/or ammonium nitrogen atom. Preferred amine compounds are those containing a tertiary nitrogen atom, e.g. trialkylamines, trialkanolamines, dialkylarylamines, diarylalkylamines, triarylamines, triaralkylamines, trialkarylamines, dialkylaralkylamines, dialkylalkarylamines, dialkylcycloalkylamines, and 5- or 6-membered heterocyclic aromatics, such as pyridine, and 5- or 6-membered heterocyclic aliphatics which include one atom of nitrogen within the ring and which may include a second atom of nitrogen or an atom of oxygen or sulfur within the ring, such as N-substituted piperidines and piperazines. Compounds containing primary and/or secondary amino groups are suitable, but such amino compounds first react with the epoxide reactant to form a tertiary alkanolamine which then behaves catalytically like other tertiary amines. Hence, there is no particular advantage in using a primary or secondary amine. Suitable amine compounds containing quaternary ammonium nitrogen are generally of the known class of tetraalkylammonium halides, which include the amino-containing ion exchange resins.

Such ion exchange resins are normally cross-linked resins bearing a plurality of tertiary amine or quaternary ammonium sites and they are typically referred to as weak base or strong base ion exchange resins. Examples of suitable amine compounds include: ammonia, butylamine, ethylenediamine, diethylenetriamine, dipropylamine, trimethylamine, triethylamine, tributylamine, trioctylamine, triethanolamine, tributanolamine, N,N-dipropylphenylamine, diphenylpropylamine, triphenylamine, triphenethylamine, tritolylamine, N,N-dimethylphenethylamine, N,N-diethylbenzylamine, N-methyl-N-hexylphenethylamine, N,N-dibutyltolylamine, N,N-diethylcyclohexylamine, piperidine, N-ethylpiperidine, N-phenylpiperidine, piperazine, N,N'-diethylpiperazine, N-phenylpiperazine, N-methylmorpholine, N-butylpyrrolidine, pyridine, tetramethylammonium chloride, tetraethylammonium bromide, ammonium chloride, and other like compounds.

Suitable iron or chromium compounds are those of the known class of iron or chromium salts and organometallic complexes that are soluble in the acid or epoxide reactants and are known to catalyze the esterification reaction. Preferred compounds are the iron and chromium halides.

Examples of suitable iron and chromium containing compounds include: $FeCl_2$, $FeCl_3$, $FeBr_3$, $CrCl_3$, ferric acetate, ferric propionate, ferric butyroate, ferric octoate, ferric dodecanoate, ferric sulfate, ferric nitrate, ferric acetylacetonate, ferric alkoxides, ferric acrylate, and other like compounds.

The subject catalyst system, as defined above, is a combination of an amine catalyst and an iron or chromium catalyst. Examples of such combinations include: triethylamine and $FeCl_3$; tributylamine and $FeBr_3$; N,N-diethylcyclohexylamine and $CrBr_3$; N,N-dimethylphenethylamine and $FeCl_3$; iron or chromium complexes with pyridine (Py) such as $Fe(Py)_4Cl_2$ and $Cr(Py)_3Cl_3$; and other like combinations.

While any ratio of the amine and iron or chromium catalyst produces a synergistic catalytic effect, the effect is best realized at a mole ratio between about 1:10 and 10:1 of (amino nitrogen):(ion of iron or chromium), and the effect is most pronounced at the preferred mole ratio which is between about 1:2 and 2:1.

The subject catalyst system is suitably present in the esterification reaction in amounts between about 0.0005 and 0.05 percent by weight, based on the weight of acid, and is preferably used in an amount between 0.001 and 0.01 percent by weight.

The amine and iron or chromium catalysts can be incorporated into the reaction mixture in any order, e.g. (a) such compounds are first mixed together and then added to either the acid or epoxide reactant, or a mixture thereof, (b) the iron or chromium compound is first dissolved in the acid reactant and the amine then added separately or in combination with the epoxide, etc. The procedure wherein the iron or chromium compound is first dissolved in the acid is generally preferred since it insures a more homogeneous mixture of catalysts and reactants. Like the amine catalysts and the iron or chromium catalysts, the carboxylic acid and vicinal epoxide reactants in the esterification reaction are generally well known.

For instance, typically suitable acid reactants include: alkane mono- or dicarboxylic acids, aromatic mono- or dicarboxylic acids, and hydroxy- or halo-substituted such acids and the like, e.g., acetic, propionic, caproic, stearic, acrylic, methacrylic, malonic, adipic, maleic, benzoic, phenylacetic, naphthenic, toluic, terephthalic, α-bromoglutaric, salicyclic, p-chlorobenzoic, m-methoxybenzoic, β-hydroxybutyric acid, and other like compounds.

Suitable epoxide reactants are generally the alkylene epoxides having 2 to 4 carbon atoms, i.e., ethylene oxide, propylene oxide and butylene oxide, and also include epihalohydrins, such as epichlorohydrin, mono and diglycidyl ethers, styrene oxide and other like compounds.

SPECIFIC EMBODIMENTS:

The following examples further illustrate the invention:

EXAMPLE 1.

Reaction Between Acrylic Acid and Ethylene Oxide Catalyzed by $FeCl_3$ and $N(CH_2CH_3)_3$.

Into each of 5 bottles was weighed 21.6 g. (0.3 mole) of freshly distilled acrylic acid (AA). $FeCl_3$ and triethylamine were sequentially added and mixed into the AA in varying amounts as indicated in Table I. Ethylene oxide (EO), 26.4 g. (0.6 mole), was then added to each bottle and mixed into the mixture. The bottles were capped, put in protective brass cages and mounted on a revolvable paddle in an 80° C. water bath. After 1 hr. in the bath, the bottles were removed and cooled to about room temperature. The bottles were opened and the volatiles removed under reduced pressure and gentle warming. The residue in each bottle, which was mainly 2-hydroxyethyl acrylate and residual acrylic acid, was weighed and titrated to a neutral pH with 0.1 N NaOH. The data of Table I is graphically presented in FIG. 1.

Table I

| Run No. | $FeCl_3$ (mols) | TEA (mols) | Ratio* | Residual Acid (%) |
|---|---|---|---|---|
| 1 | 0.001 | 0 | 1:0 | 23.8 |
| 2 | 0 | 0.001 | 0:1 | 69.0 |
| 3 | 0.0005 | 0.0005 | 1:1 | 38.2 |
| 4 | 0.00033 | 0.00067 | 1:2 | 47.5 |
| 5 | 0.00067 | 0.00033 | 2:1 | 34.6 |

*Molar ratio of $FeCl_3$ : TEA, wherein TEA is triethylamine.

EXAMPLE 2.

Figure 2:
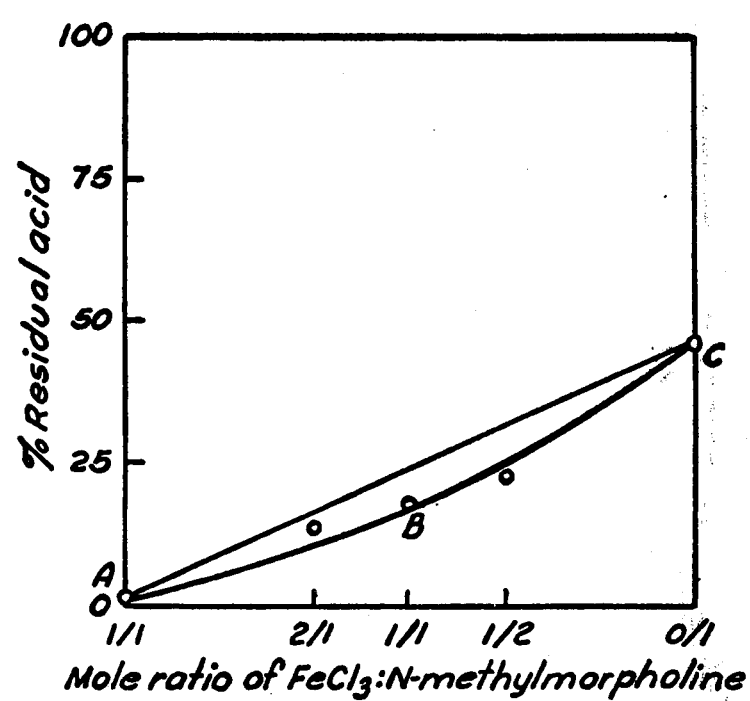

Rxn. Between Propionic Acid and Epichlorohydrin Catalyzed by a Combination of $FeCl_3$ and N-Methylmorpholine Into each of 5 bottles was weighed 23.22 g. (0.3 mole) of propionic acid (PA). $FeCl_3$ and N-methylmorpholine (NMM) were sequentially added and mixed with the acid in the amounts indicated in Table II. Epichlorohydrin (Epi), 55.5 g. (0.6 mole), was then added to each bottle and mixed into the mixture. The bottles were capped and held in an 80° C. water bath, as per Example 1, for 20 minutes after which the bottles were removed and cooled to about room temperature, uncapped, and the contents titrated with 0.1 N NaOH to a neutral pH. The data of Table II is graphically presented in FIG. 2.

Table II

| Run No. | $FeCl_3$ (mols) | NMM (mols) | Ratio* | Residual Acid (%) |
|---|---|---|---|---|
| 1 | 0.005 | 0 | 1:0 | 1.5 |
| 2 | 0 | 0.005 | 0:1 | 46.0 |
| 3 | 0.0025 | 0.0025 | 1:1 | 18.0 |
| 4 | 0.0033 | 0.0067 | 1:2 | 22.2 |
| 5 | 0.0067 | 0.0033 | 2:1 | 13.7 |

Similar synergistic catalytic results were obtained in the following reactions:

Table III

| No. | Acid Rxn. | Epoxide | Metal Salt | Catalyst System Amine |
|---|---|---|---|---|
| 1 | Terephthalic | EO | $FeCl_3$ | TEA |
| 2 | Acetic | PO* | $Fe^{+3}$(octoate) | $C_6H_5CH_2N(CH_3)_2$ |
| 3 | Acetic | PO | $Fe^{+3}$(octoate) | $C_6H_5CH_2-NH-CH_3$ |
| 4 | Acrylic | EO | $FeCl_3$ | $N(CH_3)_4Cl$ |
| 5 | Acrylic | EO | $FeCl_3$ | Amberlite 911 Resin |
| 6 | Acrylic | EO | $FeCl_3$ | Dowex 44 Resin |
| 7 | Neopentanoic | Epi | $FeCl_2$ | Pyridine |
| 8 | Oleic | Allyl Glycidyl Ether | $Fe_2(SO_4)_3 \cdot 9H_2O$ | $C_6H_5-N(CH_3)_2$ |
| 9 | Neoheptanoic | Epi | $Fe^{+3}$(acetylacetonate) | $C_6H_5-N(CH_3)_2$ |
| 10 | Acrylic | EO | Iron Acrylate | TEA |
| 11 | Acrylic | EO | $CrCl_3 \cdot 6H_2O$ | TEA |
| 12 | Acrylic | EO | $Cr(C_5H_6N)_2(H_2O)Cl$ | TEA |

*propylene oxide

Some of the above reactants in Table III are further identified as follows:

a. No. 5 - "Amberlite 911 Resin" is a commercially available quaternary amine commonly used as an ion exchange resin. The resin is cross-linked and is thought to consist of a plurality of the monomer unit

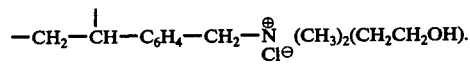

$-CH_2-CH-C_6H_4-CH_2-\overset{\oplus}{\underset{Cl^{\ominus}}{N}}(CH_3)_2(CH_2CH_2OH)$.

b. No. 6 - "Dowex 44 Resin" is a commercially available tertiary amine commonly used as a weak base anion exchange resin. The resin is cross-linked and is capable of neutralizing acids.

Other strong and weak base ion exchange resins likewise can be used. The backbone structure of the polymer in such resins is not critical and may be varied to convenience so long as the resins contain the requisite functional groups, i.e. the tertiary or quaternary amino groups. Such resins are well known to the art.

In each of paragraphs (a) and (b) above, the resin was charged into a glass column and sequentially washed with 0.1 N HCl, with water until neutral, with 10% NaOH, with water until neutral and finally washed with an aqueous solution of $FeCl_3$. The resins retained about 1–2% by weight of $Fe^{+3}$. The effectiveness of the resins as a catalyst was improved by adding the resins to a solution of acrylic acid and $FeCl_3$.

c. No. 10 - Iron acrylate was prepared by heating 5 g. of iron powder with 100 g. of glacial acrylic acid at 100° C. for 2 hrs. The solution was cooled and filtered to remove any undissolved iron. Analysis showed the solution to contain 1.2% by weight of iron.

I claim:

1. In the process of preparing a β-hydroxyester comprising reacting by contacting an organic carboxylic acid and a vicinal epoxide at a temperature between about 60° C and 130° C, the improvement comprising conducting said process in the presence of a catalytic amount of a catalytic composition comprising: (a) a first catalytic compound having at least one amino or ammonium nitrogen atom and selected from the group consisting of ammonia, ethylenediamine, diethylenetriamine, alkylamine, dialkylamine, trialkylamine, trialkanolamine, dialkylarylamine, diarylalkylamine, triarylamine, triaralkylamine, trialkarylamine, dialkylaralkylamine, dialkylalkarylamine, 5- or 6-membered heterocyclic aliphatics which include amino nitrogen within the ring, pyridine, a cross-linked ion-exchange resin bearing a plurality of tertiary amine or quaternary ammonium sites, and tetraalkyl ammonium halides, in combination with (b) a second catalytic compound, which is soluble in each of said acid and epoxide reactants, having an ionizable atom of iron or chromium and is selected from the group consisting of iron halides, chromium halides, ferric alkanoate of 1 to 12 carbon atoms, ferric sulfate, ferric nitrate, ferric alkoxides, and ferric acrylate or methacrylate; the mole ratio of (a) to (b) being from 1:10 to 10:1.

2. The process defined in claim 1 wherein said second catalytic compound is iron or chromium halide.

3. The process defined by claim 1 wherein said first catalytic compound is: ammonia, butylamine, ethylenediamine, diethylenetriamine, dipropylamine, trimethylamine, triethylamine, tributylamine, trioctylamine, triethanolamine, tributanolamine, N,N-dipropylphenylamine, diphenylpropylamine, triphenylamine, triphenethylamine, tritolylamine, N,N-dimethylphenethylamine, N,N-diethylbenzylamine, N-methyl-N-hexylphenethylamine, N,N-dibutyltolylamine, piperidine, N-ethylpiperidine, N-phenylpiperidine, piperazine, N,N'-diethylpiperazine, N-phenylpiperazine, N-methylmorpholine, N-butylpyrrolidine, pyridine, tetramethylammonium chloride, tetraethylammonium bromide, or ammonium chloride; and wherein said second catalytic compound is ferric halide, ferrous halide, chromic halide, ferric octoate, ferric sulfate, ferric acetylacetonate or ferric acrylate.

4. The process defined in claim 1 wherein said second catalytic compound is an iron halide, ferric octanoate, ferric sulfate or ferric acrylate.

5. The process defined in claim 1 wherein said first catalytic compound is triethylamine, N-methylmorpholine, benzyldimethylamine, benzylmethylamine, tetramethylammonium chloride, pyridine, phenyldimethylamine, or a cross-linked ion-exchange resin bearing a plurality of tertiary amine or quaternary ammonium sites; and wherein said second catalytic compound is iron chloride, ferric octanoate, ferric sulfate, iron acrylate, chromic chloride or a complex of pyridine and chromium chloride.

6. The process defined by claim 1 wherein said first catalytic compound is triethylamine and said second catalytic compound is ferric chloride and wherein the mole ratio of triethylamine to ferric chloride is from 1:2 to 2:1.

7. The process defined by claim 1 wherein said first catalytic compound is N-methylmorpholine and said second catalytic compound is ferric chloride and wherein the mole ratio of N-methylmorpholine to ferric chloride is from 1:2 to 2:1.

8. The process defined by claim 1 wherein said second catalytic compound is ferric acetate, propionoate, butyroate, octanoate or dodecanoate.

9. The process defined by claim 1 wherein said organic carboxylic acid is an alkane, alkene or aromatic mono- or dicarboxylic acid.

10. The process defined by claim 9 wherein said vicinal epoxide is an alkylene oxide of 2 to 4 carbon atoms, an epihalohydrin, an organic compound bearing 1 to 2 glycidyl ether moieties or styrene oxide.

11. The process defined by claim 10 wherein said organic carboxylic acid is acetic acid, propionic acid, neopentanoic acid, neoheptanoic acid, oleic acid or acrylic acid, and said vicinal epoxide is ethylene oxide, propylene oxide, epichlorohydrin or allyl glycidyl ether.

12. The process defined by claim 11 wherein said second catalytic compound is ferric acetate, propionate, butyroate, octanoate or dodecanate.

13. A process for preparing a bis(β-hydroxyalkyl) ester of an aromatic dicarboxylic acid which comprises reacting said aromatic dicarboxylic acid with a 1,2-alkylene oxide in the presence of (a) a catalyst selected from the group consisting of amines and quaternary ammonium salts, and (b) at least one iron compound which is soluble in each of said aromatic dicarboxylic acid and 1,2-alkylene oxide reactants.

14. The process defined by claim 13 wherein said aromatic dicarboxylic acid is terephthalic acid and said 1,2-alkylene oxide is ethylene oxide, propylene oxide or butylene oxide.

15. The process defined by claim 13 wherein said aromatic dicarboxylic acid is terephthalic acid.

16. The process defined by claim 15 wherein said 1,2-alkylene oxide is ethylene oxide and wherein (a) is triethylamine and (b) is ferric chloride.

* * * * *